(12) United States Patent
Ulman et al.

(10) Patent No.: US 10,980,478 B2
(45) Date of Patent: Apr. 20, 2021

(54) DEVICE FOR TISSUE CONDITION MEASUREMENT

(71) Applicant: KONINKLIJKE PHILIPS N.V., Eindhoven (NL)

(72) Inventors: Shrutin Ulman, Bangalore (IN); Sindhu Priyadarshini Nellur Prakash, Bangalore (IN); Ratheesh Narayanan, Pondicherry (IN); Shashidharan Arputha, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 293 days.

(21) Appl. No.: 15/781,868

(22) PCT Filed: Dec. 20, 2016

(86) PCT No.: PCT/EP2016/082040
§ 371 (c)(1),
(2) Date: Jun. 6, 2018

(87) PCT Pub. No.: WO2017/108869
PCT Pub. Date: Jun. 29, 2017

(65) Prior Publication Data
US 2018/0360377 A1   Dec. 20, 2018

(30) Foreign Application Priority Data
Dec. 21, 2015   (IN) .............. 6798/CHE/2015

(51) Int. Cl.
*A61B 5/00* (2006.01)
*A61B 5/145* (2006.01)
*A61B 5/1455* (2006.01)

(52) U.S. Cl.
CPC .......... *A61B 5/4878* (2013.01); *A61B 5/0035* (2013.01); *A61B 5/0053* (2013.01);
(Continued)

(58) Field of Classification Search
CPC ..... A61P 17/02; A61B 5/0205; A61B 5/0261; A61B 5/0064; A61B 5/0077; A61B 5/0095
(Continued)

(56) References Cited

U.S. PATENT DOCUMENTS

| | | | |
|---|---|---|---|
| 4,646,754 A * | 3/1987 | Seale | A61B 3/16 600/402 |
| 4,805,623 A | 2/1989 | Joebsis | |

(Continued)

FOREIGN PATENT DOCUMENTS

| | | |
|---|---|---|
| CA | 2210791 A | 1/1999 |
| CN | 104757949 A | 7/2015 |

(Continued)

OTHER PUBLICATIONS

LeGare, et al., "A Device for Measuring the Severity of Peripheral Edema", 2007.

*Primary Examiner* — May A Abouelela (57) ABSTRACT

Peripheral oedema causes a swelling of the legs of a patient due to an abnormal accumulation of fluids in the interstitium of the patient. Oedema is directly related to heart diseases, kidney and liver problems and pathological conditions. As such, is a useful indicator of a person's overall health. Oedema is typically assessed by a subjective manual test administered by a medical professional. As such, an objective assessment of oedema is often difficult to make. The present disclosure concerns a device for tissue condition measurement. The device enables an objective assessment of oedema to be made, by providing to a medical professional, or a medical ancillary worker, with information useful to judge the presence of oedema. This is achieved by performing a photoacoustic analysis of biological components present in the tissue, and then by performing a physical test by advancing a blunt instrument onto the area suspected (Continued)

of oedema, withdraw blunt instrument, and then assessing the depth and/or rebound characteristics of the pit.

8 Claims, 4 Drawing Sheets

(52) U.S. Cl.
CPC .......... *A61B 5/0095* (2013.01); *A61B 5/1455* (2013.01); *A61B 5/14546* (2013.01); *A61B 5/742* (2013.01); *A61B 2560/0431* (2013.01)

(58) Field of Classification Search
USPC .............. 600/300, 310, 322, 449, 561, 587; 606/201
See application file for complete search history.

(56) References Cited

U.S. PATENT DOCUMENTS

| | | | |
|---|---|---|---|
| 5,348,003 A * | 9/1994 | Caro | A61B 5/14546 356/39 |
| 5,553,617 A * | 9/1996 | Barkenhagen | A61B 5/14555 600/318 |
| 5,710,630 A * | 1/1998 | Essenpreis | A61B 5/14532 356/479 |
| 5,941,821 A * | 8/1999 | Chou | A61B 5/0095 600/316 |
| 6,196,231 B1 | 3/2001 | Reid | |
| 6,246,894 B1 | 6/2001 | Steuer | |
| 6,409,662 B1 | 6/2002 | Lloyd | |
| 6,484,044 B1 * | 11/2002 | Lilienfeld-Toal | A61B 5/0095 600/310 |
| 6,675,029 B2 | 1/2004 | Monfre | |
| 6,725,073 B1 * | 4/2004 | Motamedi | A61B 5/0066 600/316 |
| 6,846,288 B2 * | 1/2005 | Nagar | A61B 5/0095 600/316 |
| 7,643,858 B2 | 1/2010 | Agashe | |
| 7,645,243 B2 | 1/2010 | Lindahl | |
| 8,229,529 B2 | 7/2012 | Schmitt | |
| 8,425,433 B2 * | 4/2013 | Dunn | A61B 5/442 600/587 |
| 8,554,296 B2 * | 10/2013 | Peyman | A61B 5/0095 600/310 |
| 2005/0107709 A1 | 5/2005 | Hampel | |
| 2006/0030791 A1 | 2/2006 | Billiar et al. | |
| 2006/0270935 A1 * | 11/2006 | Ariff | G06Q 10/06398 600/437 |
| 2007/0179365 A1 | 8/2007 | Bitton | |
| 2007/0179389 A1 * | 8/2007 | Wariar | G16H 40/67 600/508 |
| 2009/0043229 A1 | 2/2009 | Dunn | |
| 2011/0035232 A1 * | 2/2011 | Forbes | A61K 31/7016 705/2 |
| 2012/0179006 A1 * | 7/2012 | Jansen | A61B 5/0537 600/301 |
| 2014/0018649 A1 * | 1/2014 | Jespersen | A61B 5/4064 600/322 |
| 2014/0066786 A1 * | 3/2014 | Naghavi | A61B 5/4836 600/481 |
| 2014/0121495 A1 * | 5/2014 | Dempsey | A61B 5/4848 600/411 |
| 2014/0296749 A1 * | 10/2014 | Reid, Jr. | D04B 1/265 600/587 |
| 2015/0046183 A1 * | 2/2015 | Cireddu | G06F 19/3418 705/3 |
| 2015/0094548 A1 | 4/2015 | Sabatini et al. | |
| 2015/0099980 A1 | 4/2015 | Nahman | |
| 2016/0073949 A1 * | 3/2016 | Grant | A61B 5/0059 600/301 |

FOREIGN PATENT DOCUMENTS

| | | |
|---|---|---|
| JP | 2008093158 A | 4/2008 |
| WO | 2013/153743 | 10/2013 |
| WO | 2015/048639 | 4/2015 |

* cited by examiner

DEVICE FOR TISSUE CONDITION MEASUREMENT

CROSS REFERENCE TO RELATED APPLICATIONS

This application is the U.S. National Phase application under 35 U.S.C. § 371 of International Application No. PCT/EP2016/082040, filed Dec. 20, 2016, published as WO 2017/108869 on Jun. 29, 2017, which claims the benefit of Indian Patent Application Number 6798/CHE/2015 filed Dec. 21, 2015. These applications are hereby incorporated by reference herein.

FIELD OF THE INVENTION

This invention relates to a device for tissue condition measurement, a system for tissue condition measurement, a method for tissue condition measurement, a computer program element, and a computer-readable medium. More particularly, this invention relates to an approach for communicating information about tissue conditions.

BACKGROUND OF THE INVENTION

A trend in medical technology is towards providing equipment which provides information about the condition of a patient in a standardized way. This information is utilized by a medical professional in the course of their duties.

Peripheral oedema is a swelling of the legs of a patient due to an abnormal accumulation of fluids in the interstitial tissues. An assessment of peripheral oedema is a useful indicator of a person's health, because it is related to heart disease, kidney and liver problems, and pathological conditions. Oedema can be classified, for example, as pitting, or non-pitting oedema. Traditionally, pitting oedema has been distinguished from non-pitting oedema using a manual test. In this test, pressure is applied to a patient's swollen leg, leaving a physical depression in the swollen leg. The depth, and rebound time of the pit provides information enabling a distinction between pitting and non-pitting oedema.

U.S. Pat. No. 8,425,433 B2 discusses approaches to provide further information about peripheral oedema, but such methods can be further improved.

SUMMARY OF THE INVENTION

According to a first aspect of the invention, there is provided a device for tissue condition measurement.

The device comprises:
a light source configured to emit light onto a region of interest of a patient;
a light receiver configured to receive light emitted from the light source and subsequently reflected from the region of interest;
a sound receiver configured to receive sound waves emitted from the region of interest;
a pressure application unit configurable between a refracted position and an advanced position, wherein the transition of the pressure application unit between the retracted position and the advanced position causes pressure to be applied to the region of interest;
a processing unit; and
a communications interface.

The processing unit is configured to obtain tissue component information at a region of interest of a patient using the light source and the sound receiver, wherein the processing unit is configured to cause the pressure application unit to apply a pressure to the region of interest by advancing the pressure application unit between the retracted position and the advanced position, to withdraw the pressure application unit from the region of interest, and to obtain pit rebound information at the region of interest.

The communications interface is configured to communicate the tissue component information, and the pit rebound information.

Therefore, according to the first aspect, information about tissue condition can be accurately obtained, and communicated to a medical professional, or ancillary staff, for further analysis. Pit rebound information and tissue component information is obtained from a region of interest of a patient through a standardized approach, enabling a more accurate provision of information about the condition of tissue at the region of interest of the patient. Such information can enable a medical professional, or ancillary staff, to reach a more accurate diagnosis of a condition such as oedema.

According to an embodiment of the first aspect, the device is provided wherein the tissue component information comprises a first and a second tissue component value, and the pressure applied by the pressure application unit is calculated based on a ratio of the first and second tissue component values.

Accordingly, the tissue component information and the pit rebound information is more accurate, because the condition of the tissue at the region of interest of the patient is used to generate the pressure applied to the region of interest by the pressure application unit. Thus, the pressure application unit applies a pressure to a patient which is suitable for obtaining accurate results for that particular patient.

According to an embodiment of the first aspect, there is provided a device for tissue condition measurement wherein the light source and the sound receiver are configured to detect at least a water component and a haemoglobin component at the region of interest, and wherein the first tissue component value is the detected water component, and the second tissue component value is the detected haemoglobin component.

According to this embodiment, the characterization of the tissue in terms of the ratio of water and haemoglobin contained in the tissue may be used to control the pressure applied to a patient in a subsequent oedema classification step.

According to an embodiment of the first aspect, the light source is configured to emit light in the wavelength ranges of (i) 380 nm to 470 nm, (ii) 545 nm to 600 nm, and (iii) 1200 nm to 1400 nm.

According to this embodiment, wavelengths having an distance of tissue penetration into different depths of patient tissue are used.

According to an embodiment of the first aspect, the pit rebound information comprises a pit depth value, and/or a pit rebound time value measured at the region of interest.

According to this embodiment, an oedema condition may be classified accurately following the application of a constant pressure to the region of interest of a patient.

According to an embodiment of the first aspect, the pit depth value and/or the pit rebound time is obtained using an optical proximity sensor.

According to this embodiment, the pit depth value and/or the pit rebound time may be measured using a simple and accurate approach.

According to a second aspect, there is provided a system for tissue condition measurement. The system for tissue condition measurement comprises:
- a device for tissue condition measurement according to the first aspect and its embodiments, and
- a computer.

The computer is communicatively coupled to the communications interface of the device for tissue condition measurement, the computer is configured to obtain tissue component information and pit rebound information at a region of interest of a patient, and the computer is configured to use the tissue component information and the pit rebound information to provide a tissue condition assessment at the region of interest of the patient.

According to an embodiment of the second aspect, a system is provided according to the second aspect, further comprising:
- a display unit communicatively coupled to the computer.

According to a third aspect, a method for tissue condition measurement is provided. The method comprises:
a) obtaining tissue component information using photoacoustic spectroscopy at a region of interest of a patient;
b) generating tissue characterization information of the region of interest based on the obtained tissue component information;
c) applying a pressure to the region of interest by advancing a pressure application unit between a retracted position and an advanced position;
d) withdrawing the pressure application unit from the region of interest;
e) obtaining pit rebound information at the region of interest; and
f) communicating the tissue component information and the pit rebound information via a communications interface.

According to the third aspect, tissue condition may be assessed at a region of interest of a patient in a standardized and accurate way.

According to an embodiment of the third aspect, the method of the third aspect is provided, wherein the tissue component information comprises a first and a second tissue component value, and wherein the pressure applied by the pressure application unit is calculated based on the ratio of the first and second tissue component values.

Accordingly, pressure may be applied to the region of interest of a patient based on a characterization of the tissue at the region of interest of a patient.

According to an embodiment of the third aspect, there is provided the further step g):
g) combining the tissue characterization information and the tissue classification information to provide a tissue condition assessment at the region of interest of the patient.

The tissue condition assessment can be used to provide standardized information to a medical professional useful in the ultimate assessment of the risk that a patient is afflicted by a certain type of oedema.

According to an embodiment of the third aspect, a method is provided according to the third aspect or any of its embodiments, further comprising the step f1) of displaying the tissue condition assessment to a user.

According to an embodiment of the third aspect, a method according to the third aspect or its embodiments is provided, wherein the pit rebound information comprises a pit depth value, and/or a pit rebound time value, measured at the region of interest of the patient.

According to a fourth aspect of the invention, there is provided a computer program element for controlling a processing unit and/or a computer as claimed in one of the first or second aspects, which, when the computer program element is executed by the processing unit and/or computer, is adapted to perform the method of the third aspect.

According to a fifth aspect of the invention, there is provided a computer-readable medium having stored the computer program element of the fourth aspect.

In the following description, the term "tissue condition measurement" means the characterization of quantities describing skin tissue of a patient using standardized means, enabling useful assessment of the condition of the patient skin to be made by a medical professional or a medical ancillary worker.

In the following description, the term "tissue component information" concerns one or a plurality of measurements providing an indication of the amount of various biological substances present in the skin of a patient. For example, human skin contains components such as melanin, water, and haemoglobin located at different depths in the epidermis, dermis, or subcutaneous tissue. Tissue component information is an indication of the relative amounts of such materials in the skin at the region of interest of a patient. In an example, these components can be derived by photoacoustic spectroscopy. Further analysis of the tissue component information may enable tissue at the region of interest of a patient to be characterized. As discussed below, the tissue component information can be considered to cover "raw" unprocessed sound received after the application of light to the region of interest, or processed sound, because the tissue information is still derivable from the "raw" sound.

In the following description, the term "photoacoustic spectroscopy" means the indirect measurement of the effect of a light source incident on a region of interest of a patient. The technique works by shining a light on the region of interest. Tissues on, or in, the region of interest emit sounds as a result of the application of the light. For each light wavelength, different tissues emit sound with a different acoustic signature (spectrum). Such a photoacoustic spectrum of a sample is recorded by measuring the spectrum, or detecting for certain sound components emitted from a region of interest at the application of one, or several wavelengths of incident light. In an example, a light source and a sound receiver enable a distinction to be made between different amounts of water, melanin, or haemoglobin in human skin.

It will be appreciated that the term "photoacoustic spectroscopy" covers a situation where one, or a plurality of relatively narrowband light sources are used either in turn, or in combination, to target specific materials in a region of interest. For example, a first specific light source for targeting melanin in human skin could be activated, and the magnitude of the sound response recorded. In turn, a second specific light source for targeting haemoglobin could be activated, and the magnitude of the sound response recorded. This provides photoacoustic spectroscopy at certain absorbed light wavelengths of interest.

Alternatively, or in addition, a plurality of light sources at wavelengths of interest could be activated in unison, and the ensemble of the sound responses recorded for further analysis, with the analysis (such as a filter bank, or a Fast Fourier Transform (FFT) providing the levels of material components at the region of interest. Of course, broadband photoacoustic spectroscopy, in which a white light source is emitted towards the region of interest, and the broadband sound response is recorded for further analysis, such as by a filter bank or FFT, is also applicable.

In the following description, the term "pit rebound information" means information about the static and/or dynamic behaviour of the tissue of a patient at the region of interest. When pressure is applied to tissue at the region of interest by advancing the pressure application unit, a pit is formed in the tissue. Measurement of the pit depth (the deepest deviation of the pit for a given applied pressure, compared to the usual skin level), and/or whether or not the pit rebounds instantly, not at all, or rebounds over a shorter or longer time period, enables classification of a condition such as oedema as either "pitting" or "non-pitting". Thus, the "pit rebound information" may be a depth measured in millimetres, for example. Alternatively, or in addition, the "pit rebound information" may index the depth measurement to time, to provide a rebound characteristic.

Thus, it can be considered to be a basic idea to characterize tissue at a region of interest of a patient according to the relative levels of different components of biological substances, for example water, haemoglobin or melanin. Then, a classification of the tissue at the region of interest of a patient is provided by applying pressure to the region of interest, and obtaining information about the static or dynamic behaviour of the tissue at the region of interest of a patient. Processing the gathered information separately, or together, enables more accurate information about the condition of tissue in the region of interest of the patient to be presented to a medical professional. In addition, because a standard device is used to perform these measurements, the information presented to the medical professional is more accurate, thus enabling the medical professional to come to a more accurate diagnosis of, for example, oedema. Less experienced staff can, additionally, be aided when checking patients for the condition.

BRIEF DESCRIPTION OF THE DRAWINGS

Exemplary embodiments will be described with reference to the following drawings.

DETAILED DESCRIPTION OF EMBODIMENTS

Peripheral oedema is a swelling of interstitial tissues of the body, usually the legs, of a patient. The swelling is due to an accumulation of fluid in interstitial tissues. Peripheral oedema is an indicator of many conditions, such as heart disease, kidney failure, and liver failure. Oedema can be characterized in terms of biological substances present in the epidermis, dermis, and hypodermis such as haemoglobin, melanin and water. Knowledge of the ratios of these substances can enable a more accurate characterization of oedema.

Melanin glands are, typically, present in the boundary between epidermis and dermis. Blood vessels present in the dermis layer can be used to indicate the presence of haemoglobin. Visible light can be used to estimate the ratios of different components in the skin, and it is seen from FIG. 1a) that different wavelengths of light penetrate to different depths in the human skin.

Figure 1A:
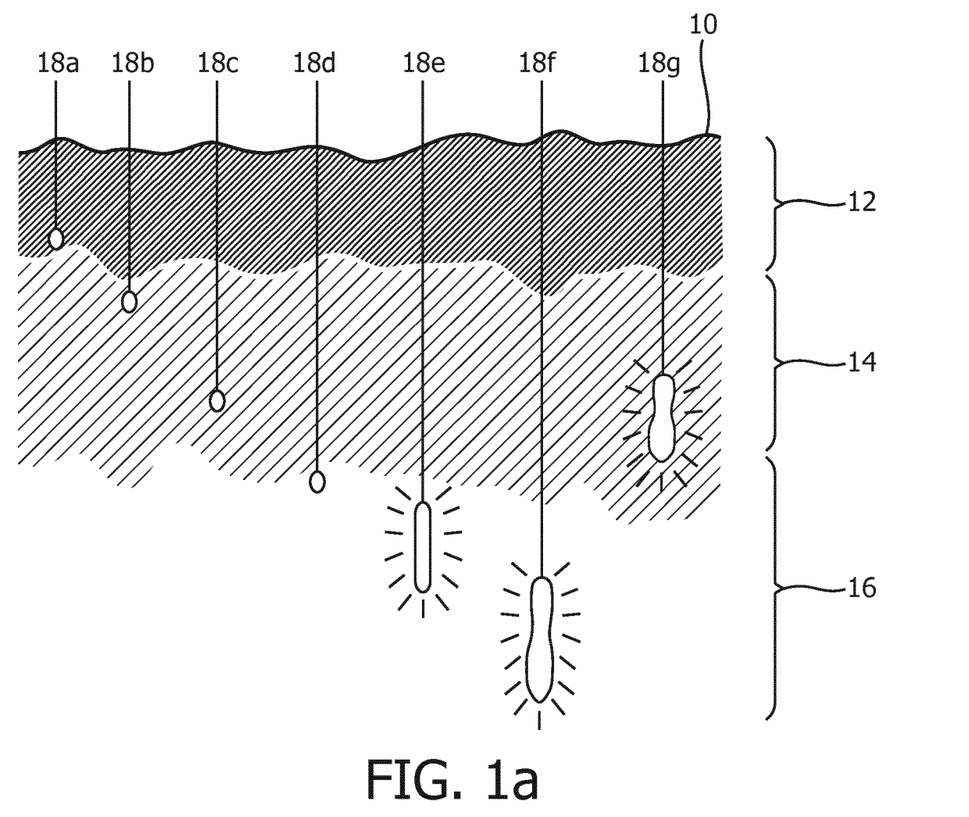
FIG. 1a) shows a cross-sectional view of a human skin with the light penetration depth of various wavelengths of light superimposed.

FIG. 1a) shows a section through human skin showing three important layers, and the relative penetration of different wavelengths of light therein, for constant beam power. From the surface of the skin 10, the first layer is the epidermis 12, the second layer is the dermis 14, and the third layer is the hypodermis 16. The characterization of oedema may be enhanced by locating the presence of components such as melanin, water, and haemoglobin in neither layers of the skin.

In FIG. 1a), beam 18a is in the 150 nm to 380 nm wavelength range, representing ultra-violet radiation, which has a penetration of about 0.1 mm. Beam 18b is in the wavelength 390 nm to 470 nm, the violet-deep blue colour, and has a penetration into the skin of 0.3 mm. Beam 18c lies in the wavelength range of 475 nm to 545 nm, in other words the blue-green range, and penetrates the skin to a depth of between 0.3 mm and 0.5 mm in depth. Ray 18d represents light in the wavelength range 545 nm to 600 nm, having the colour yellow to orange. This penetrates between 0.5 mm and 1 mm into the dermis layer. Ray 18e represents light in the red colour range at 600 nm to 650 nm. It penetrates between 1 mm and 2 mm into the hypodermis 16. Ray 18f is a deep red or near infrared ray penetrating between 2 mm and 3 mm into the skin. Finally, near infrared rays are shown at 18g penetrating less far into the skin, typically only reaching the dermis.

Hence, it can be seen that by using light of different wavelengths to examine the skin, information about different layers of the skin and their composition can be obtained.

Figure 1B:
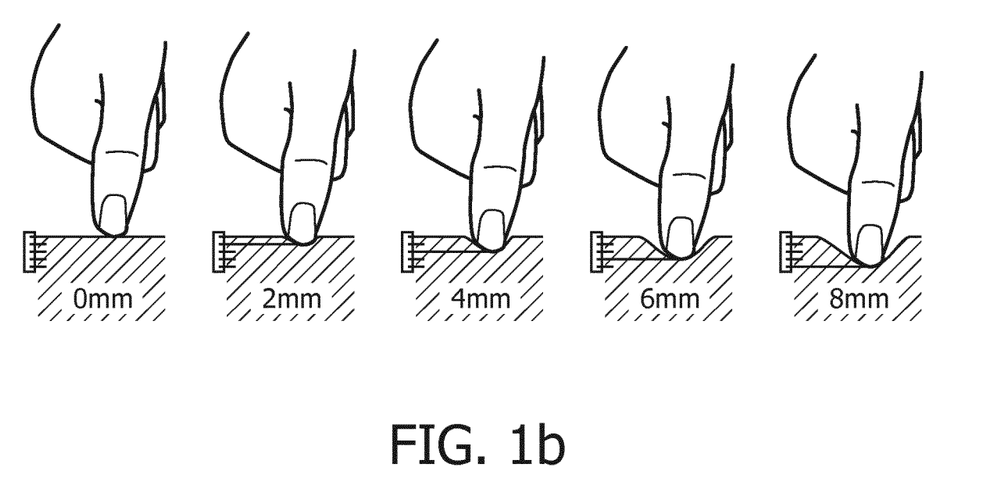
FIG. 1b) shows a standardized oedema classification approach involving the application of a human hand to an area afflicted with oedema.

FIG. 1b) shows a traditional approach to characterizing oedema as "pitting" or "non-pitting". In this approach, a physician depresses the skin of a patient at a region of interest using their finger. After pressing the skin down, the physician removes their finger. The second scenario from the left of FIG. 1b) shows a mildly pitting oedema, in which a 2 mm depression is produced which disappears rapidly. A moderately pitting oedema is defined as one which is 4 mm deep, and disappears between ten to fifteen seconds after the pressure is removed. Moderately severe pitting oedema is considered to be indicated by a 6 mm depression that endures for 1 minute. Severely pitting oedema is considered to be indicated by an 8 mm depression that can last for more than two minutes.

It will be understood that the subjectivity involved in the quantification of pitting oedema by the application pressure can lead to inaccuracies in diagnosis. Extensive training is required to derive useful information about the condition of the patient, using the manual method.

Automated techniques for providing information about the condition of the under-skin region are available. Ultrasound imaging has been used as a technique for identifying oedema. Spectrophotometry has also been applied to differentiate oedema, as compared to internal bleeding. However, ultrasound cannot distinguish well between all of the tissue components useful for characterizing oedema. Spectrophotometry has a relatively low resolution, because the optical scattering in soft tissues is more pronounced than the scattering of sound waves.

Therefore, according to a first aspect of the invention, there is provided a device for tissue condition measurement which enables information useful for characterizing and classifying oedema to be presented to a medical professional, or ancillary staff, for further analysis.

Figure 2:
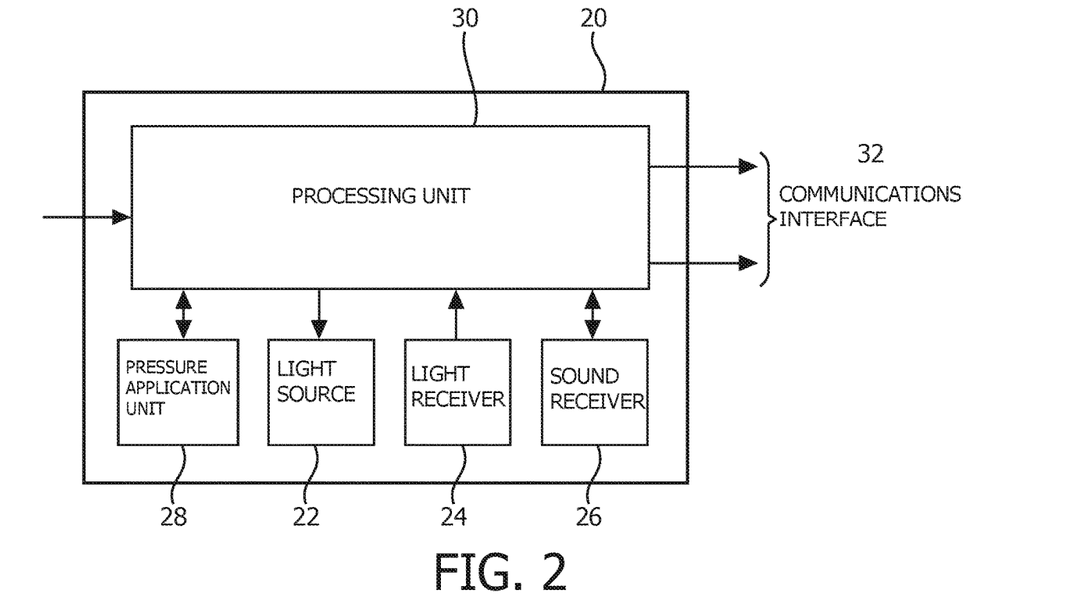
FIG. 2 shows a device for tissue condition measurement according to the first aspect.

According to a first aspect, there is provided a device 20 for tissue condition measurement. The device comprises:
- a light source 22 configured to emit light onto a region of interest of a patient;
- a light receiver 24 configured to receive light emitted from the light source 22 and subsequently reflected from the region of interest;
- a sound receiver 26 configured to receive sound waves emitted from the region of interest;
- a pressure application unit 28 configurable between a retracted position and an advanced position, wherein the transition of the pressure application unit 28 between the retracted position and the advanced position causes pressure to be applied to the region of interest;
- a processing unit 30; and
- a communications interface 32.

The processing unit 30 is configured to obtain tissue component information at a region of interest of a patient using the light source 22 and the sound receiver 26. The processing unit 30 is configured to cause the pressure application unit 28 to apply a pressure to the region of interest by advancing the pressure application unit 28 between the retracted position and the advanced position, to withdraw the pressure application unit 28 from the region of interest, and to obtain pit rebound information at the region of interest. The communications interface 32 is configured to communicate the tissue component information, and the pit rebound information.

Accordingly, information about the tissue condition of a patient can be accurately obtained, and communicated to a medical professional, or ancillary staff, for further analysis.

FIG. 2 illustrates a high level block diagram of the device for tissue condition measurement according to the first aspect, showing a device 20 having a light source 22, a light receiver 24, a sound receiver 26, a pressure application unit 28, a processing unit 30, and a communications interface 32.

The light source 22 provides light of suitable wavelengths at the region of interest of the patient. For example, the light source 22 may be one, or multiple, light emitting diodes (LEDs) configured to emit light of suitable wavelengths onto the patient. Alternatively, lasers could be used. The wavelengths of the applied light is/are typically chosen to correspond to the optical response components of human tissue which are of interest to medical professionals.

The light receiver 24 is configured to receive light applied by the light source 22 and reflected from a region of interest patient. For example, the light receiver is a photodiode, a photo-transistor, or a photo-Darlington transistor. Optionally, the light receiver 24 may be filtered to receive certain wavelengths of light.

The sound receiver 26 is a microphone, for example an "electret" microphone or a MEMS microphone configured to receive sound waves emitted from the region of interest of the patient.

Typically, the light source 22, the light receiver 24, and the sound receiver 26, are located at a distal end of the device 20, enabling them to be put close to, or in contact with, the region of interest.

The light source 22, and sound receiver 26 may, for example, be used in a photoacoustic spectroscopy approach to provide tissue component information of the skin at the region of interest. In the device 20, the light source 22 may be directed to emit light at a region of interest of a patient. A photoacoustic sound emission is received by the sound receiver 26, and processed by the processor 30. In some embodiments, the sound is transmitted via the communications interface 32 to enable further analysis of the tissue components in a remote device. In other embodiments, the processor 30 of the device 20 performs the photoacoustic spectroscopy, and transmits the result via the communications interface.

The light source 22, and the light receiver 24 may, for example, be used as an optical proximity sensor. A light signal applied to a patient by the light source 22 and reflected from a region of interest of a patient will be received with greater strength at the light receiver 24 as the surface of the skin at the region of interest moves closer to the light receiver 24.

The pressure application unit 28 applies pressure to the region of interest to classify the oedema as pitting or non-pitting, and/or to determine the degree of oedema. The pressure application unit is typically a blunt, piston-type instrument provided at the distal end of the device for tissue condition measurement (the proximal end is held by the user).

The pressure application unit 28 is configured to be actuated, for example, by an electromechanical system such as a servomechanism, or a motor arranged to drive a nut and lead-screw arrangement, although other mechanisms will be known to the skilled person. The pressure application unit is configurable between the retracted position, where the device 20 for tissue condition measurement will have a minimum length, and the advanced position, in which the device 20 for tissue condition measurement will have its greatest length. This enables the application of a predictable pressure to a region of interest of a patient, when the device 20 is held close to the region of interest.

The device 20 comprises a processing unit 30. The processing unit may be a microprocessor, a field programmable gate array, a digital signal processor, or custom logic configured to control the light source 22, the light receiver 24, the sound receiver 26, and the pressure application unit 28, and to communicate information obtained from the light receiver 24 and the sound receiver 26 via the communications interface 32 for further analysis.

The communications interface 32 is provided to enable communication of the results of a tissue condition measurement from the device 20 to an external device, computer, or smartphone for further analysis. The communications interface is, in an example, a Bluetooth™ or a Wi-Fi™ wireless communications interface. In another example, the communications interface is a wired communications interface such as a wired USB link.

In operation, the device 20 for tissue condition measurement is placed against, or in close proximity to, a region of interest of a patient for which the provision of tissue condition information is desired. For example, the patient's legs may be examined.

The user of the device 20 then actuates the device into a tissue characterization stage. In the tissue characterization stage, tissue component information is obtained by shining the light source 22 at the region of interest, and by receiving sound at the sound receiver 26. The light source 22 emits light, at one or a plurality of wavelengths, onto the region of interest of a patient.

The sound received is generated at the region of interest by the photoacoustic effect, which is the formation of sound waves following the penetration of light into a material sample, in this case the skin of the patient.

The sound receiver 26 receives sound waves emitted from the region of interest of a patient. The processing unit gathers the signals from the sound receiver 26 as tissue component information.

The device 20 is then actuated into a tissue characterization stage. With the device still in contact with the region of interest, the pressure application unit 28 is configured to be actuated to advance a blunt end from a retracted position to an advanced position of the device 20 in such a way as to apply a pressure to the region of interest, causing a "pit" to be formed at the region of interest.

The pressure application unit 28 then withdraws the blunt end from the advanced position to the retracted position of the device 20.

At the time of the refraction, or shortly after it, the light source 22 is activated, and used with the light receiver 24 as an optical proximity detector. As the pit surface normalizes to the average skin surface, an increasing amount of light from the light source 22 is reflected into the light receiver 24, causing a received light signal to have a higher magnitude. By tracking the change in the received light signal, pit rebound information may be obtained. The change may be a change in the magnitude of the received light. Optionally, the light source 22 is "strobed" in synchrony with measurements of the light receiver 24, to enable an uncorrelated sequence of depth measurements to be obtained.

Then, the tissue component information and the pit rebound information is communicated via communications interface 32.

It will be appreciated that light source 22 and sound receiver 26 are together used as a photoacoustic spectroscope ultimately to provide tissue component information, but that "raw" or intermediate information may be processed in different locations, and then be combined to form a final photoacoustic spectroscopy result. Photoacoustic spectroscopy has several advantages over existing spectroscopic methods. The spatial resolution of photoacoustic spectroscopy is greater than that of the spectrophotometry, because photoacoustic spectroscopy detects the sound waves produced by optical absorbers, rather than detecting back-scattered light. In addition, the scattering of acoustic waves is almost three times lower than the scattering of optical signals, in soft tissues. Therefore, the resolution of photoacoustic spectroscopy is approximately three times higher than that of spectrophotometry.

Photoacoustic spectroscopy can be used to distinguish between different components present in oedema, unlike ultrasound approaches. Therefore, photoacoustic spectroscopy allows functional and structural imaging. The present application discusses using the photoacoustic spectroscopy method to determine and to characterize the presence of different components such as haemoglobin, melanin and water in tissue fluids present beneath the skin, although other components can be targeted. Therefore, tissue component information can be provided which can enable the characterization of oedema.

As discussed previously, human skin is made up of three important layers: the epidermis, dermis, and hypodermis. Components of common substances such as melanin, water, and haemoglobin need to be located in these layers.

Melanin glands are present between the dermis and the epidermis. Thus, using light in the wavelength range 380 nm to 470 nm can be used to estimate the presence of melanin. Blood vessels are present in the dermis layer, and so the wavelength range of 545 nm to 600 nm can be used to estimate the presence of haemoglobin. The wavelength range of 1200 nm to 1400 nm can be used to estimate the presence of water.

Thus, the acoustic signal strength sensed by the sound receiver, compared to the intensity of the precursor emitted light, provides an estimate of the light absorbed by the different tissue components.

The abundance of a tissue component is proportional to the ratio between the signal strength from the acoustic transducer, and the intensity of the incident light with a wavelength which targets that component.

It will be appreciated that the device 20 records "raw" sound information emitted from the region of interest using the sound receiver 26. The "raw" sound information is the input for the photoacoustic spectroscopy approach. In one example, a single light source 22 of a specific wavelength may be actuated, and first "raw" sound information obtained. In another example, a plurality of light sources having different wavelengths may be actuated sequentially, or in ensemble. Second "raw" sound information may be obtained of this sequence, or ensemble. The first and/or second "raw" sound information then undergoes a processing step to obtain its spectrum. For example, a digital signal processing technique may be used to obtain the spectrum of the "raw" sound information. An example Digital Signal Processing (DSP) technique is the "Fast Fourier Transform" (FFT).

Another approach which may be applied when obtaining the tissue component information is simply to actuate light sources having different wavelengths of interest for detecting melanin, water, and haemoglobin, and to measure the magnitude of the sound received from the region of interest with the actuation of each light source. This approach allows simpler, or no signal processing to be used. In this case, the tissue component information is the sequential magnitude of each sound received by the sound receiver 26 after the sequential actuation of each light source 22. This "reduced complexity" approach means that simpler signal processing circuitry is required.

The intensity of the acoustic waves reflected by the region of interest is detected by the sound receiver. According to an embodiment, the ratio of signal strength sensed by the acoustic transducer to the emitted light intensity provides an estimate of the amount of light absorbed by the tissue components.

Having obtained the "raw" sound information, it may be compared to standard values of different tissue components in order to characterize the spectrum as being characteristic of a region of interest having a high haemoglobin content, for example.

At this point, it is necessary to recognize that there are many locations where the processing of the "raw" sound information to form the photoacoustic spectrum, and the comparison of the photoacoustic spectrum with the standard values of different tissue components, can be performed. Additionally, the spectrum need not be a smooth spectrum, but may only have a few data points necessary to identify the required skin components. Therefore, the present application considers the term "tissue component information" to embrace (i) the "raw" sound information, (ii) "raw" sound information after signal processing, and (iii) processed "raw" sound information, which has been compared to standard values of different tissue components to provide tissue characteristic information. The term "tissue component information" may be considered to embrace these three possibilities because the tissue component ratios are derivable from (i) and (ii), as well as being explicitly provided in (iii).

It will also be appreciated that a system employing the technique described herein may be partitioned in different ways, with the required processing occurring in different system components, with substantially the same technical effect.

In an embodiment, the device 20 collects the "raw" sound information, performs the signal processing on the "raw" sound information, and compares the processed "raw" sound information to standard values of different tissue components held on the device itself to provide tissue characteristic information. This is, then, communicated via the communications interface 32. This may be termed a "standalone device" embodiment, in which more processing power is needed on the device 20, and the "standard values of different tissue components" need to be stored or updated onto the device itself. However, in this embodiment, no external devices are required, and the communication interface 32 may itself comprise a screen or indicator held on the body of the device 20, to provide analysis information to a medical professional.

In another embodiment, the device 20 collects the "raw" sound information, and transmits the "raw" sound information as tissue component information over the communications interface 32 to an external computing device (such as a smartphone). Optionally, the "raw" information is compressed in the device 20, and decompressed in the external computing device. The external computing device performs the signal processing on the "raw" sound information, and compares the digitally processed "raw" sound information to standard values of different tissue components held on the external computing device, to enable the display of updated tissue component information to a user on the external computing device.

In an embodiment, the external computing device is configured to download updates of the standard values of different tissue components from a remote server, and/or to send them to the device 20.

In an embodiment, the device 20 collects the "raw" sound information, and transmits the "raw" sound information as tissue component information over the communications interface 32 to an external computing device (such as a smartphone). The external computing device performs the signal processing on the "raw" sound information. This "intermediate" tissue component information is transmitted via a network or Wide Area Network, such as the internet, to a "cloud"-based analysis service. The "cloud"-based analysis service analyzes the "intermediate" tissue component information, to provide tissue component information, which is transmitted back to the external computing device for display to a user. Alternatively, or in addition, the tissue component information may be transmitted to a database holding patient information.

Therefore, it will be appreciated that, although a photoacoustic spectroscopy approach is ultimately used to derive the tissue component information, it is not essential for all processing operations relating to that photoacoustic spectroscopy to be performed entirely by the device 20.

According to an embodiment, the pressure applied by the pressure application unit 28 is calculated based a first tissue component value of the tissue component information.

In this embodiment, the pressure applied by the pressure application unit 28 is customized to the requirement of a patient, based upon the prior determination of a first tissue component value of the region of interest. For example, if tissue at the region of interest is found to have a certain percentage of water content, the pressure application unit 28 may be configured to apply a certain pressure to the region of interest in Pascals, for a certain time, as a response. In this case, the tissue component information is used to address a look-up table, or a mathematical model defining, for a certain tissue component distribution, what pressure should be applied to a patient. It will be appreciated that this determination could be made on the device 20, an external computer, or in a "cloud"-based system.

This enables more appropriate measurements of pitting or non-pitting oedema to be made, based on an appropriately calculated pit depth.

According to an embodiment, the pressure application unit 28 is configured to apply a constant pressure.

According to an embodiment, the tissue and component information comprises a first and a second tissue component value. The pressure applied by the pressure application unit 28 is calculated based on the ratio of the first and second tissue component values.

Optionally, a look-up table is provided comprising pressure application information indexed by values of the first and/or second tissue component values.

According to an embodiment of the device 20, the light source 22 and the sound receiver 26 are configured to detect at least a water component and a haemoglobin component at the region of interest, and the first tissue component value is the detected water component and the second tissue component value is the detected haemoglobin component.

Thus, pit rebound information is obtained by extending the pressure application unit to an advanced position, and the retracting it to a retracted position. The blunt structure is recoiled, and a light source 22 is activated constantly, or at time intervals. Subsequently, the light receivers 24 of the blunt structure give reflected signal values.

As the pit recoils back towards the blunt structure in its refracted position, the reflected signal received at the light receiver will become stronger. Effectively, this means that the light source 22 and the light receiver 24 act as an optical proximity sensor. The time taken by the sensed signal value to be equal to a reference value recorded before the application of the blunt instrument of the region of interest gives the rebound time. The difference between the change of reflected intensity value just after the recoil of the pen, and the initial reference value can be used to calculate the pit depth information. With the help of the pit depth and the pit rebound time, the oedema can be classified as either pitting or non-pitting. If classified as pitting, the degree of pitting oedema can be provided. Thus, the device 20 is also configured to provide pit rebound information.

Having the tissue component information and the pit rebound information, The "degree of oedema" is characterized as the ratio between the percentage of water in the tissue, and the percentage of haemoglobin in the tissue.

In an embodiment, based on the pit depth, and the pit rebound time, and a comparison to standardized values, the oedema can be classified as "pitting" or "non-pitting".

According to an embodiment, the tissue component information and the pit rebound information may be combined and compared to standard values, to provide an overall oedema assessment value.

Figure 3A:
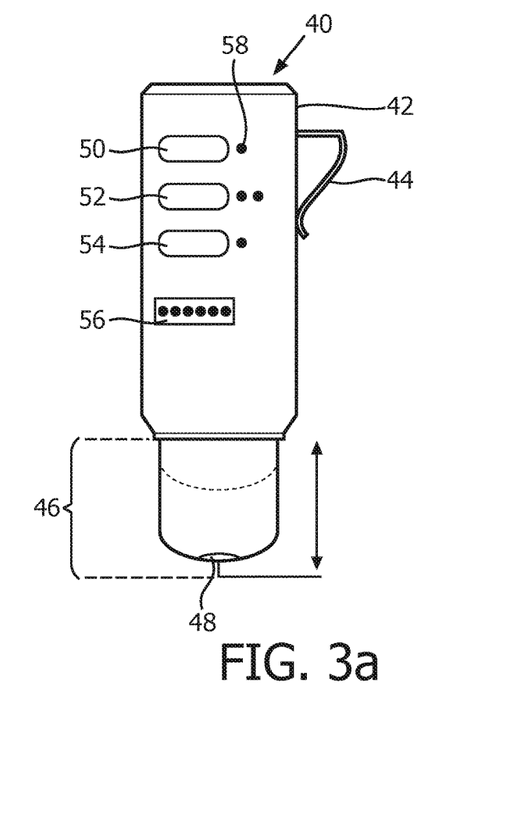
FIG. 3a) shows a side view of an exemplary device for tissue condition measurement.
Figure 3B:
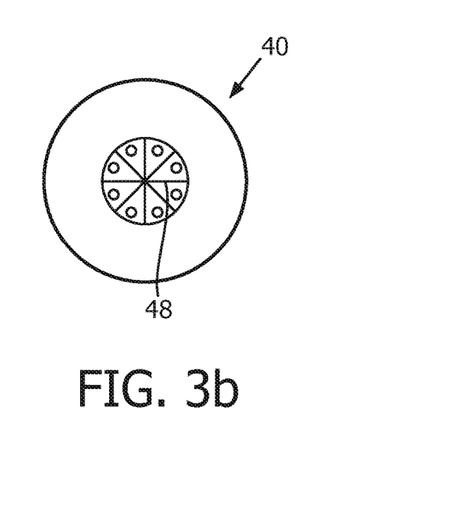
FIG. 3b) shows a distal end view of an exemplary device for tissue condition measurement.

FIG. 3a) and FIG. 3b) show a device for tissue condition measurement according to an exemplary embodiment. FIG. 3a) shows a side view of a device for tissue condition measurement 40. FIG. 3b) shows a distal end view of a device for tissue condition measurement 40, in which the distal end is used to make contact with the region of interest of a patient.

The illustrated embodiment of the device for tissue condition measurement 40 shown in FIGS. 3*a*) and 3*b*) comprises a cylindrical, pen-like enclosure 42 which may optionally have a clip at the proximal end for attaching to the uniform of a medical professional. The distal end of the pen comprises a retractable measurement section 46 comprising a blunt structure corresponding to the pressure application unit 28 previously discussed. The tip 48 of the pressure application unit comprises a light and sensor module 48. The light and sensor module 48 comprises at least one light source (for example, an LED), at least one light receiver (for example, a photodiode or photo-transistor) and a sound receiver (such as a MEMS microphone or an "electret" microphone).

When held in the proximity of, or touching, a region of interest of a patient, the blunt structure, and the light source, light receiver, and sound receiver come close to, or contact, the region of interest, enabling tissue component information to be measured by the light source and the sound receiver in the tip 48. The pressure application unit 46 is configurable between a retracted position and an advanced position. In the illustration of FIG. 3*a*), the pressure application unit 46 is shown in the advanced position using continuous lines, and in the retracted position using dotted lines.

The device 40 optionally comprises a first button 50 to power the oedema pen "on" or "off". The device 40 optionally contains a second button to start the oedema examination process. The device 40 optionally contains a third button 54 which, when pressed, enables tissue component information and pit rebound information to be transmitted to an external computer for further analysis. The device 40 optionally comprises a battery monitor 56 for monitoring the battery life of the device 40. The outside of the casing of the device optionally also contains a plurality of LEDs 58 for illustrating when the pen is powered on or off, when an examination is in progress or completed.

FIG. 3*b*) shows the distal end of the device 40 of the present exemplary embodiment from an end-on position at the distal end. The light and sensor module 48 comprises radially distributed LEDs, a sound receiver 49, and a light receiver 47. It will be appreciated, though that many arrangements of these components may be provided, while still allowing information to be obtained from the region of interest of the patient. For example, the light sources (LEDs) could be arranged around the circumference of the tip 48, and the sound receiver 49 arranged in the middle of the tip 48.

Figure 4:
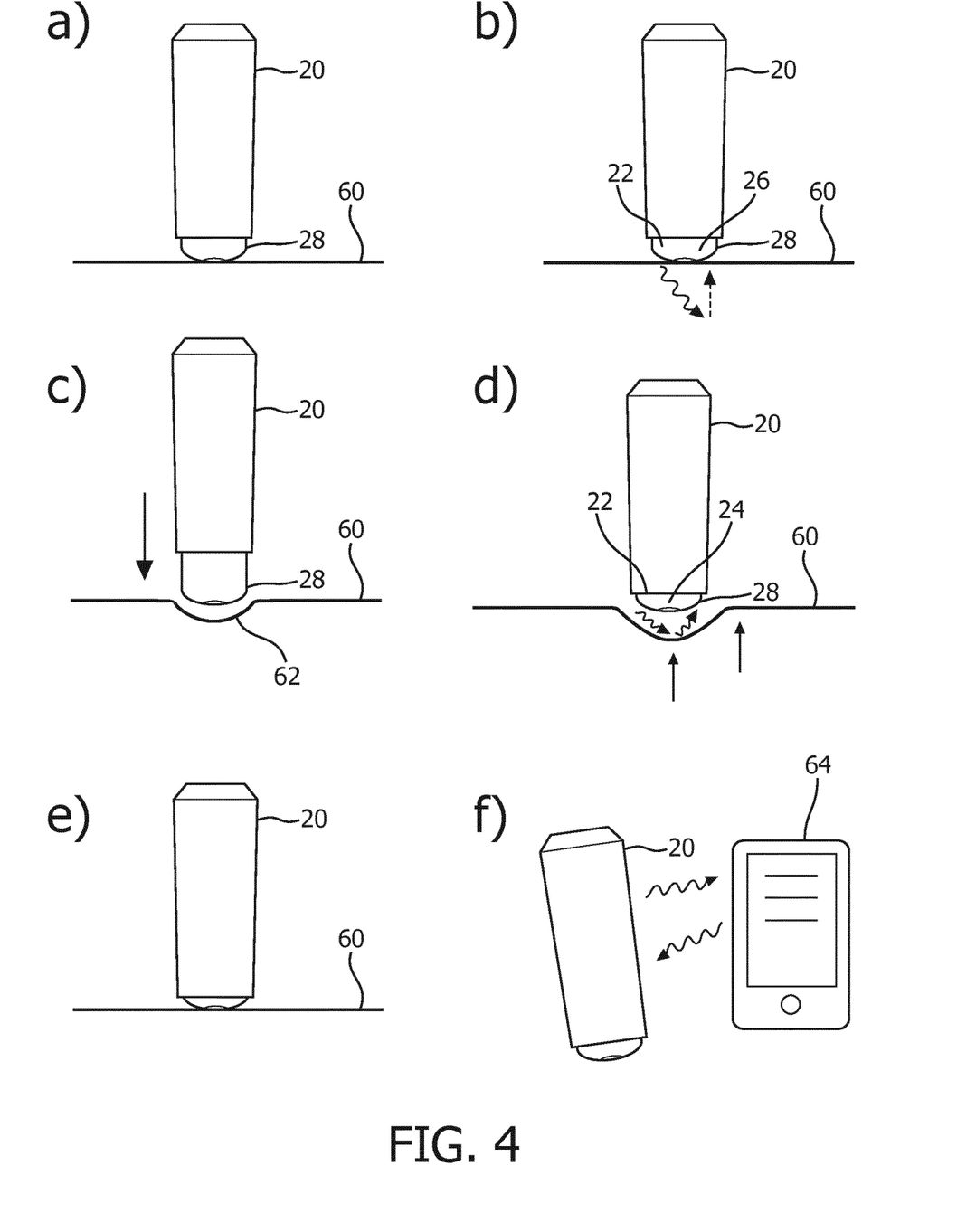
FIG. 4 shows stages in the use of the exemplary device for tissue condition measurement.

FIG. 4 shows stages in the examination of a patient using the device for tissue condition measurement according to the exemplary embodiment of FIG. 3.

In FIG. 4*a*), the device 20 is placed against the surface of a skin region 60 of a patient suspected of oedema. The blunt structure forming the pressure application unit 28 is in a retracted position.

FIG. 4*b*) shows a first stage of obtaining tissue component information after activation of the device by a user. The light source 22 in the retracted pressure application unit 28 of the device 20 is in contact, or close to, the surface of the patient skin 60. The light source emits light at one, or a plurality of wavelengths into the region of interest. The sound receiver 26 receives sound waves emitted from the skin of a patient. An exemplary light wave is shown as the solid wavy line, and the dotted line represents the emission of sound back into the sound receiver unit 26 from skin 60.

Thus, LEDs, optionally of one, or of different wavelengths, characterizing the tissue components are activated to emit incident light onto the skin 60. The sound receiver receives the sound waves emitted by the skin. The ratio of incident light intensity to the calculated sound waves is calculated. A characterization of different types of oedema may be provided by finding the ratio of presence of different tissue components.

FIG. 4*c*) shows the next stage of the examination, having obtained the tissue component information, wherein the processing unit of the device 20 causes the blunt end of the pressure application unit 28 to be extended into the surface of the skin of a patient skin, causing a pit 62 to be formed in the skin of the patient. Typically, the pit will be between 1 and 10 mm in depth.

FIG. 4*d*) shows the next stage of the examination, where the device 20 has retracted the pressure application unit 28. Because the blunt end of the pressure application unit 28 has been withdrawn, natural rebound forces in the skin will press under the surface of the skin 60 to cause the generated pit to be equalized gradually to the level of the remainder of the surface of the skin. The time, and optionally dynamic rate at which this process occurs is monitored by the light source emitting light into the pit, and the light receiver 24 receiving reflections of the light from the bottom of the pit.

FIG. 4*e*) shows the situation where the measurement is complete, and the surface of the skin 60 is in a straight position, substantially touching the device for tissue condition measurement 20.

FIG. 4*f*) shows a final step optional step comprising transmission of information between the device 20 and an external computer 64 via a communications interface 32. It will be appreciated that the final step is not essential, and information may instead be processed on the device 20. Optionally, the device 20 transmits an audible signal designating the end of the test.

The pressure application unit 28 of the device 20 delivers an amount of pressure to a point on the patient.

According to an embodiment, the amount of pressure to be applied at the region of interest is calculated based on a first and a second tissue component value.

According to an embodiment of the invention, the first tissue component value is the amount of water at the region of interest, and the second tissue component value is the amount of haemoglobin at the region of interest. Thus, the pressure applied at the region of interest can be customized based on the ratio of tissue components detected in the skin.

According to an embodiment of the invention, the device 20 is provided, wherein the light source is configured to emit light in the wavelength ranges of 380 nm to 470 nm, 545 nm to 600 nm, and 1200 nm to 1400 nm.

According to an embodiment, the pit rebound information comprises a pit depth value, and/or a pit rebound time value measured at the region of interest.

According to an embodiment, a device is provided, wherein the pit depth value and/or the pit rebound time is obtained using an optical proximity sensor.

Figure 5:
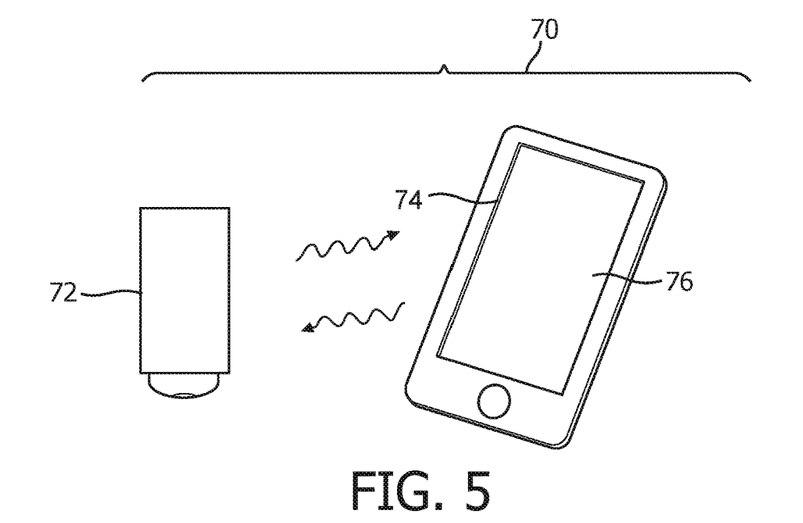
FIG. 5 shows a system for tissue condition measurement according to the second aspect.

According to a second aspect, a system 70 is provided which enables tissue condition measurement. The system comprises a device for tissue condition measurement 72 as previously described according to the first aspect or its embodiments, and a computer 74 wherein the computer is communicatively coupled to the communications interface of the device 72 for tissue condition measurement. In an example, the computer 74 is a smartphone.

The computer 74 is configured to obtain tissue component information and pit rebound information at a region of interest of a patient. The computer 74 is configured to use the tissue component information and pit rebound information to provide a tissue condition assessment at the region of interest of the patient.

According to this aspect, the device 72 collects tissue information and pit rebound information from a patient. A remote device 74 performs tissue condition assessment using the tissue component information and pit rebound information.

For example, the computer 74 receives tissue component information and pit rebound information and then compares the values to standard values in a look-up table, before arriving at a tissue condition assessment of, for example, the oedema status of the patient.

According to an embodiment of the second aspect, the computer is provided with a display unit 76.

Figure 6:
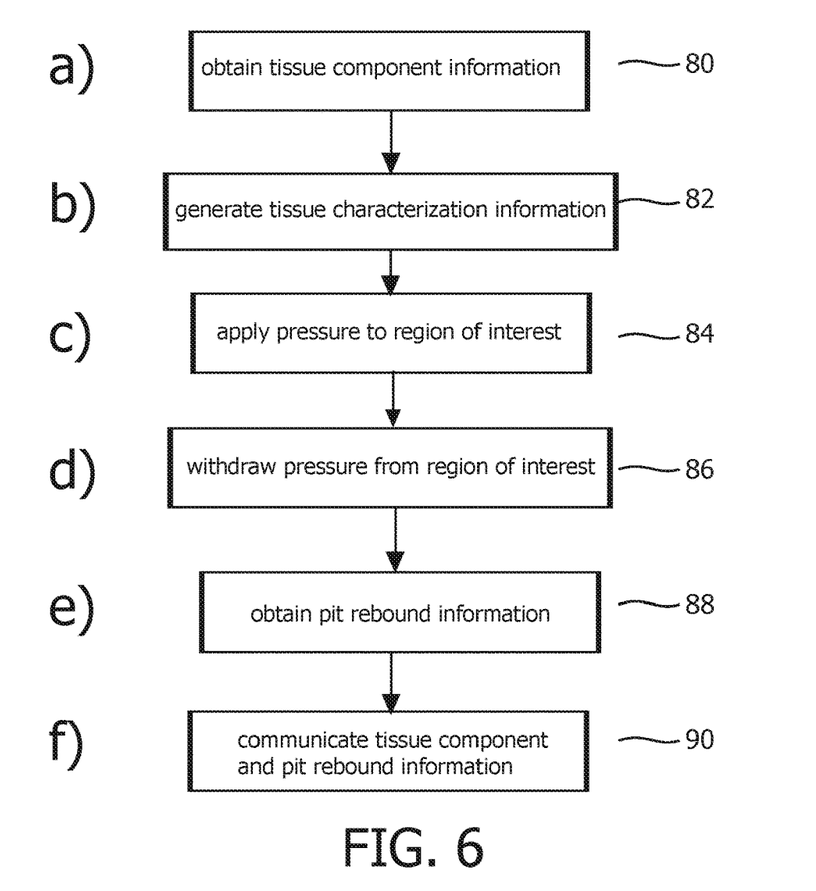
FIG. 6 shows a flow-diagram of a method for tissue condition measurement according to the third aspect.

According to a third aspect, there is provided a method for tissue condition measurement. The method comprises:
a) obtaining 80 tissue component information using photoacoustic spectroscopy at a region of interest of a patient;
b) generating 82 tissue characterization information of the region of interest based on the obtained tissue component information;
c) applying 84 a pressure to the region of interest by advancing a pressure application unit between a retracted position and an advanced position;
d) withdrawing 86 the pressure application unit from the region of interest;
e) obtaining 88 pit rebound information at the region of interest; and
f) communicating 90 the tissue component information and the pit rebound information via a communications interface.

According to an embodiment of the third aspect, the tissue component information comprises a first and a second tissue component value, wherein the pressure applied by the pressure application unit is calculated based on the ratio of the first and second tissue component values.

According to an embodiment of the third aspect, the method of the third aspect further comprises
g) combining the tissue characterization information and the tissue classification information to provide a tissue condition assessment at the region of interest of the patient.

According to an embodiment of the third aspect, the method as provided previously comprises:
h) displaying the tissue condition assessment to a user.

According to an embodiment of the third aspect, a method is provided as described previously, wherein the pit rebound information comprises a pit depth value and/or a pit rebound time value measured at the region of interest.

According to a fourth aspect, there is provided a computer program element for controlling a processing unit and/or a computer as claimed in the above device embodiments which, when the computer program element is executed by the processing unit and/or computer, is adapted to perform one of the embodiments above.

According to a fifth aspect, a computer-readable medium having stored the computer program element of the fourth aspect is provided.

It will be noted that the above-stated steps may also be executed in a different order. For example, the tissue component information may be communicated to the communications interface directly after it has been received, and before measurement of the pit rebound information.

The computer program element might be stored on a computer unit, which might also be part of an embodiment of the present invention. This computing unit may be adapted to perform or induce the performance of the steps described above. Moreover, it may be adapted to operate the components of the above-described apparatus. The computing unit can be adapted to operate automatically, and/or to execute the orders of a user. A computer program may be loaded into the working memory of a data processor. The data processor may, thus, be equipped to carry out the method of the third aspect.

This exemplary embodiment covers both the computer program which is configured to use the invention initially, or a computer program that is configured from an existing program into a program that uses the invention by means of a software update, for example.

The computer program element is thus able to provide all necessary steps necessary to fulfill the procedure required according to the third aspect discussed above.

According to a further exemplary embodiment of the present invention, a computer-readable medium, such as a CD-ROM, is presented, wherein the computer-readable medium has a computer program element stored on it, wherein the computer program element is described in the previous section.

A computer program may be stored and/or distributed on a suitable medium, such as an optical storage medium or a solid-state medium supplied together with, or as a part of the hardware. The computer-readable medium may also be distributed in other forms, such as via the Internet, or as a wired or wireless telecommunication system.

The computer program can also be presented over a network like the World Wide Web, and can be downloaded into the working memory of a data processor from such a network. According to a further exemplary embodiment of aspects of the present invention, a medium for making a computer program element available for downloading is provided, which computer program element is arranged to perform a method according to one of the previously described embodiments of the invention.

It should be noted that embodiments of the invention are described with reference to subject-matter that is different. In particular, some embodiments are described with reference to method-type features, whereas other embodiments are described with respect to apparatus-type features. A person skilled in the art will gather from the above, and following description, that unless otherwise notified, in addition to any combination of features belonging to one type of subject-matter, also any other combination between features belonging to one type of subject-matter is considered to be disclosed within this application. All features can be combined to provide a synergetic effect, which is more than the simple summation of the features.

Whilst the invention has been illustrated and described in detail in the drawings and foregoing description, such illustration and description are to be considered to be illustrative or exemplary, and not restrictive. The invention is not limited to the disclosed embodiments.

Other variations to the disclosed embodiments can be understood, and effected, by those skilled in the art in practicing the claimed invention, from a study of the disclosure and the drawings, the description, and the dependent claims.

In the claims, the word "comprising" does not exclude other elements or steps. The indefinite article "a" or "an" does not exclude a plurality. A single processor, or the unit, may fulfil the functions of several items recited in the claims. The mere fact that certain measures are recited in mutually different dependent claims does not indicate that a

The invention claimed is:

1. A device for tissue condition measurement comprising: a light source configured to emit light onto a region of interest of a patient; a light receiver configured to receive light emitted from the light source and subsequently reflected from the region of interest;
- a sound receiver configured to receive sound waves emitted from the region of interest;
- a pressure application unit having a blunt piston instrument at a distal end thereof, configurable between a retracted positon and an advanced position, wherein a transition of the pressure application unit between the retracted position and the advanced position configured to cause the blunt instrument at the distal end thereof to apply pressure to the region of interest when the device is held close to the region of interest, causing a pit to be formed at the region of interest;
- a processing unit; and
- a communications interface;
- wherein the processing unit is configured to obtain tissue component information at the region of interest of the patient using the light source and the sound receiver, wherein the processing unit is configured to cause the pressure application unit to apply a pressure to the region of interest by advancing the pressure application unit between the retracted position and the advanced position, to withdraw the pressure application unit from the region of interest, and to obtain pit rebound information at the region of interest, and
- wherein the communications interface is configured to communicate the tissue component information, and the pit rebound information.

2. The device of claim 1,
wherein the tissue component information comprises a first and a second tissue component value; and wherein the pressure applied by the pressure application unit is calculated based on a ratio of the first and second tissue component values.

3. The device of claim 2,
wherein the light source and the sound receiver are configured to detect at least a water component and a haemoglobin component at the region of interest, and wherein the first tissue component value is the detected water component, and the second tissue component value is the detected haemoglobin component.

4. The device according to claim 1,
wherein the light source is configured to emit light in at least one of a wavelength ranges of (i) 380 nm to 470 nm, (ii) 545 nm to 600 nm, and (iii) 1200 nm to 1400 nm.

5. The device according to claim 1,
wherein the pit rebound information comprises a pit depth value and/or a pit rebound time value measured at the region of interest.

6. The device according to claim 5,
wherein the pit depth value and/or the pit rebound time is obtained using an optical proximity sensor.

7. A system for tissue condition measurement comprising:
- a device for tissue condition measurement according to claim 1; and
- a computer;
- wherein the computer is communicatively coupled to the communications interface of the device for tissue condition measurement;
- wherein the computer is configured to obtain the tissue component information and the pit rebound information at the region of interest of the patient; and
- wherein the computer is configured to use the tissue component information and the pit rebound information to provide a tissue condition assessment at the region of interest of the patient.

8. The system of claim 7, further comprising:
a display unit communicatively coupled to the computer.

* * * * *